United States Patent [19]

Drinkard et al.

[11] Patent Number: 5,374,767
[45] Date of Patent: Dec. 20, 1994

[54] PROCESS FOR THE PRODUCTION OF CYCLOHEXYLADIPATES AND ADIPIC ACID

[75] Inventors: William C. Drinkard, Wilmington, Del.; Gerald C. Grunewald; Ronald Reimer, both of Orange, Tex.

[73] Assignee: E. I. Du Pont de Nemours and Company, Wilmington, Del.

[21] Appl. No.: 204,053

[22] Filed: Mar. 2, 1994

Related U.S. Application Data

[63] Continuation-in-part of Ser. No. 46,912, Apr. 15, 1993, Pat. No. 5,321,155.

[51] Int. Cl.$^5$ .................................................. C07C 67/035
[52] U.S. Cl. ....................................................... 560/193
[58] Field of Search ............................... 560/193, 191

[56] References Cited

U.S. PATENT DOCUMENTS

| | | | |
|---|---|---|---|
| 3,564,051 | 2/1971 | Haarer et al. | 562/524 |
| 3,767,720 | 10/1973 | Drinkard | 200/607 |

FOREIGN PATENT DOCUMENTS

| | | | |
|---|---|---|---|
| 51-36267 | 10/1976 | Japan | 560/193 |
| 1402480 | 8/1975 | United Kingdom | 562/524 |

*Primary Examiner*—James H. Reamer

[57] ABSTRACT

Cyclohexyladipates are formed in a staged reactor, e.g. a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

9 Claims, 1 Drawing Sheet

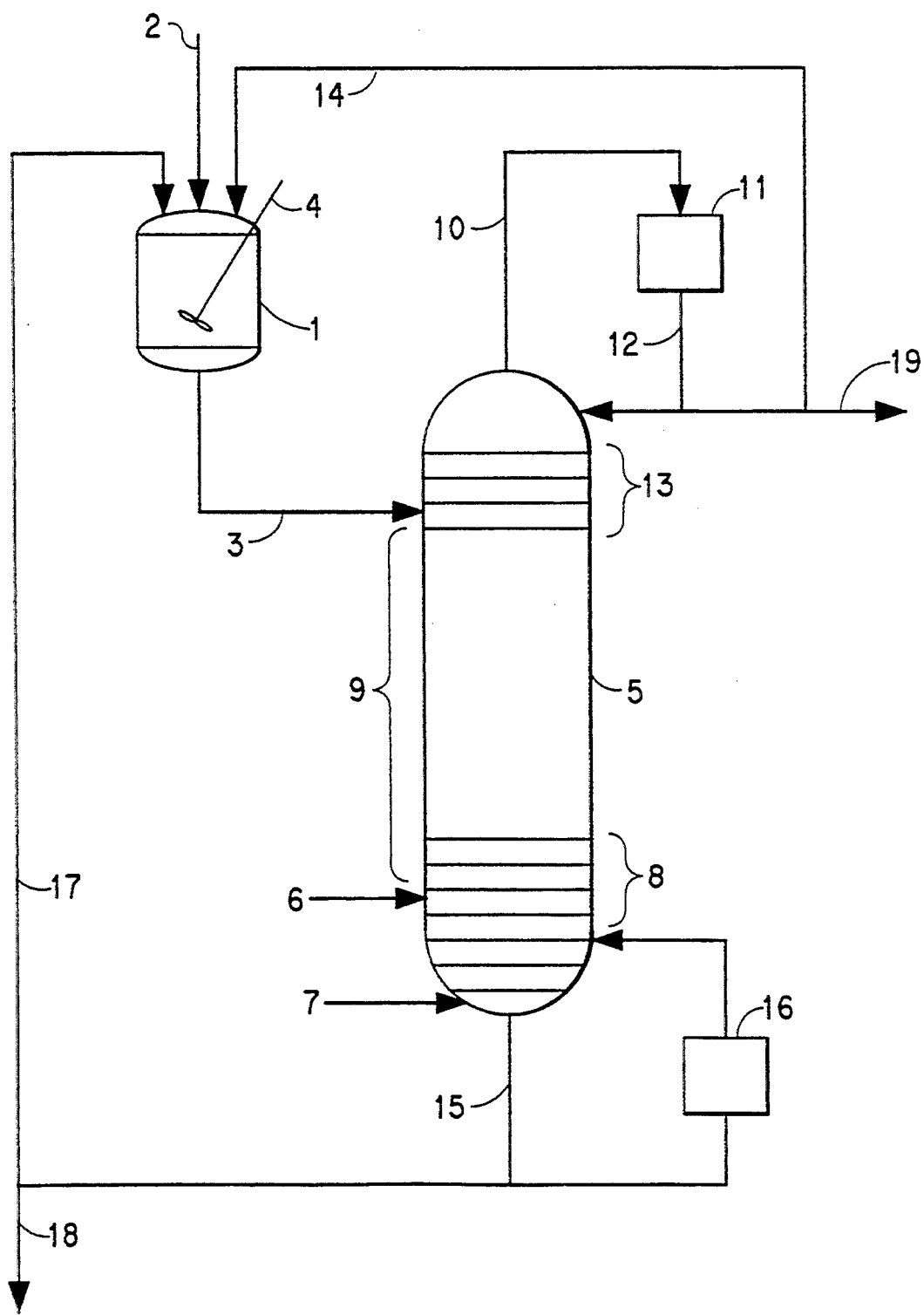

PROCESS FOR THE PRODUCTION OF CYCLOHEXYLADIPATES AND ADIPIC ACID

REFERENCE TO EARLIER APPLICATION

This application is a continuation-in-part of U.S. patent application Ser. No. 08/046,912 filed Apr. 15, 1993.

FIELD OF THE INVENTION

This invention relates to the production of cyclohexyladipates by the reaction of a mixture containing benzene, cyclohexene and adipic acid to form a mixture of mono- and di-cyclohexyladipates (called herein cyclohexyladipates), and also to the conversion of the thus formed cyclohexyladipates to adipic acid by nitric acid oxidation.

BACKGROUND OF THE INVENTION

A conventional method for the manufacture of adipic acid is the air oxidation of cyclohexane to form a mixture of cyclohexanone and cyclohexanol. This mixture is then oxidized with nitric acid to adipic acid.

The preparation of adipic acid is also carried out commercially by the selective hydrogenation of benzene to form cyclohexene, separation of the cyclohexene from the unconverted benzene and the overhydrogenated species cyclohexane, by extractive distillation, then hydration of cyclohexene to form cyclohexanol, and the nitric acid oxidation of the cyclohexanol to adipic acid. See for example Kagaku Kogaku (Chemical Technology), vol. 55, No. 5, pp 382-385 (1991); "Technology for Manufacturing Cyclohexanol using Cyclohexene Technique" by Shikazo Senoo and Koji Nakagawa.

British Patent 1,402,480 teaches the preparation of adipic acid by esterification of cyclohexene with adipic acid using an acid catalyst, and then oxidizing the cyclohexyladipates with nitric acid to form adipic acid.

Japanese published patent application 51-36,267 (Published Oct. 7, 1976) discloses that cyclohexyladipates may be formed by the reaction of cyclohexene and adipic acid using an acid catalyst. The published application states: "The cyclohexene used in the present invention may be conventional-grade cyclohexene; the presence of a small amount of inert substances such as cyclohexane and benzene does not present a problem."

SUMMARY OF THE INVENTION

The present invention is a process for the production of cyclohexyladipates in a staged reaction zone containing an acid catalyst, said staged reaction zone having a upper portion and a lower portion, said staged reaction zone having a temperature above about 100 degrees C. and at a pressure greater than 50 psig, which comprises (a) feeding to the lower portion of the staged reaction zone a mixture containing a major amount of benzene, and a minor amount of cyclohexene, (b) feeding to the upper portion of the staged reaction zone, adipic acid, (c) removing cyclohexyladipates from the lower portion of the staged reaction zone, and (d) removing benzene from the upper portion of the staged reaction zone. The cyclohexyladipates, if desired, may be converted to adipic acid by nitric acid oxidation.

The present invention is thus able to use as the feed stock the reaction material obtained by the partial hydrogenation of benzene. See Drinkard U.S. Pat. No. 3,767,720. No separation of the cyclohexene is required. The present process also eliminates the hydration of cyclohexene to cyclohexanol and cyclohexanone. Furthermore, in the present process after preparation of the cyclohexyladipates by use of acid catalysts, the separation of the cyclohexyladipates from the other components is simplified. The present invention allows direct nitric acid oxidation of the cyclohexyladipates to form adipic acid.

The process is attractive because of satisfactory conversions and yields: this process operates at 2-20 times the conversion rate of traditional cyclohexane oxidation systems and it has a 10-25% higher yield to adipic acid.

BRIEF DESCRIPTION OF THE DRAWING

The FIGURE is of a schematic illustration of apparatus arranged to carry out the process of the invention.

DETAILED DESCRIPTION

There are many known processes for the preparation of cyclohexene by the partial hydrogenation of benzene. The Drinkard patent is an example. Most of the known processes employ ruthenium as a catalyst. These processes produce a reaction mixture containing benzene, cyclohexene and cyclohexane. To avoid the formation of large amounts of cyclohexane, it is necessary to operate the processes at benzene conversions of about 50% or less, which results in a selectivity to cyclohexene of as high as about 80%, and a selectivity to cyclohexane of about 20%. If less benzene is converted, the selectivity to cyclohexene is greater. For the process of the present invention a feed stream of about 80% benzene, 18% cyclohexene, and 2% cyclohexane is preferred.

In accordance with the present invention, a feed stream containing major amounts of benzene, and minor amounts of cyclohexene is reacted with an adipic acid stream in the presence of a catalytic amount of an acid catalyst. The adipic acid stream may contain components other than adipic acid, such as cyclohexyladipates, and may be partly a recycle stream. Preferred acid catalysts include acidic silica alumina, tin tetrachloride, zinc dichloride, vanadium oxide ($V_2O_4$), p-toluenesulfonic acid, acid ion exchange resins such as Nafion® or Amberlite 200®, acidic molecular sieve resin, and heteropolyacids. Both Lewis acids and Bronsted acids may be satisfactory. A preferred Lewis acid is zinc dichloride. The amount of catalyst needed will usually be in the range of about 1-100 parts per million parts of the reaction mixture when the catalyst is in the reactants. The acid catalyst may be contained in either or both feed streams; it may be fed to the reaction zone as a separate stream or the staged reaction zone may be packed with solid particulate catalytic material, e.g. acid ion exchange resin. The adipic acid in the reaction mixture should be present in at least a stoichiometric amount necessary to form the mono-cyclohexyladipate. Excess adipic acid is often desirable. Some di-cyclohexyladipate will form even at high ratios of adipic acid to cyclohexene.

The phrase "major amount of benzene" means that benzene is present in the reaction mixture in an amount substantially in excess of the amount of cyclohexene. Thus the phrase "minor amount of cyclohexene" means that cyclohexene is present in the reaction mixture in an amount substantially less than the amount of benzene. Normally the ratio of benzene to cyclohexene in the reaction mixture is in the range of about 3 to 1 to about 6 to 1. The reaction mixture will normally also have 1 to 10% by weight cyclohexane.

The formation of the cyclohexyladipates is carried out at a temperature above about 100 degree C. Temperatures as high as 210 degrees C. are satisfactory.

The cyclohexyladipate-formation process step is carried out under pressure. Pressures greater than 50 psig are required. Pressures up to 200 psig are satisfactory.

The reaction of adipic acid with cyclohexene to form the esters, cyclohexyladipates, is an equilibrium reaction. The reaction does not go to completion in a single stage.

In a staged reaction zone, for example a reactive distillation column, adipic acid is added at the top where it comes into contact with benzene/cyclohexane containing very low concentrations of cyclohexene. The high concentration of adipic acid reacts with most of the remaining traces of cyclohexene to form cyclohexyladipates. The overhead stream is mostly benzene plus cyclohexane and is very low in cyclohexene.

Near the bottom of the column a feed stream containing a major amount of benzene and a minor amount of cyclohexene is introduced into the column. At this point the concentration of adipic acid is low, and the cyclohexene reacts to minimize the amount of adipic acid leaving the reaction zone. In this manner most of the adipic acid is consumed and mixture high in cyclohexyladipate concentration exits the bottom of the column.

An advantage of this system is that there is a very low amount cyclohexene in the recycle benzene to be separated and returned to the reactor, and a very low amount of adipic acid in the cyclohexyladipates to be fed to nitric oxidation.

In essence, a staged reaction zone such as a reactive distillation column is like a series of reactors in which one of the reactive components enters one end and the other reactive component enters from the other end and they flow counter-current to each other. Both components are reacted nearly to completion even though they would normally exist in equilibrium with the product in a single stage.

The nitric acid oxidation can be carried out in the same reactor and under the same conditions that are usually employed for the oxidation of cyclohexanone and cyclohexanol in the formation of adipic acid: i.e. the nitric acid concentration is about 20 to 80% and the reaction temperature is about 40 to 120 degrees C. (See British patent 1,402,480 page 3 column 2 for details.)

EXAMPLES

A 60 ml stainless steel autoclave is charged with the following mixture: 10.0 g of benzene, 8.0 g of cyclohexene, 2.0 g of cyclohexane, 15.0 g of adipic acid, and 40 mg of $ZnCl_2$. This system is heated to 130 deg. C. at an initial cold pressure of 50 psig for 1 hour. 3.0 g of cyclohexyladipates were formed.

The entire reaction mixture is distilled at atmospheric pressure at 83 deg. C. which separates the unreacted benzene, cyclohexene, and cyclohexane from the higher boiling cyclohexyladipates and unreacted adipic acid. This tails mixture of cyclohexyladipates and adipic acid is oxidized with $HNO_3$ to convert to entirely adipic acid.

A semimicro oxidation flask (50 ml) fitted with a serum stoppered feed point, thermometer, condenser, magnetic stirrer and heating mantle was charged with 20 ml (27.21 g) of 58% nitric acid (0.5% Cu, 0.5% V). This charge was spiked with about 5 mg sodium nitrite and heated to 85° C., then 1.502 g of cyclohexyladipates (68% mono-cyclohexyladipate, 32% di-cyclohexyladipate) was injected below the stirred liquid surface over a 17 minute period at a temperature of 86° C. (+ or −1° C.). The 85° C. temperature was held 10 minutes after ester addition was completed then the solution temperature was quickly increased to 98°–100° C. and held for 5 minutes.

The product was analyzed and the yield to dibasic acids was determined by subtracting the adipic acid content of the esters from the total adipic acid in the product in order to determine the moles of adipic formed by oxidation of the cyclohexyl portion of the esters. The yield to adipic acid was 95% with 3.5% glutaric acid and 1.5% succinic acid. This yield is equivalent to the yield obtained in a similar nitric oxidation using cyclohexanol and cyclohexanone as a feed rather than cyclohexyladipates.

Best Mode Contemplated

The process of the invention to continuously synthesize a mixture containing mono- and di-cyclohexyladipates is contemplated to be operated in a reactive distillation column 5 which will operate at 120°–180° C. The primary feed stream 3 above the catalytic reactive section 9 of the reactive distillation column will contain 10–50% adipic acid, dissolved in a mixture containing benzene and cyclohexyladipates, and will be prepared in a heated dissolution tank 1. Feeds to the dissolution tank will include recycled benzene 14, make up adipic acid 2 (from a standard nitric acid oxidation process), and a mixed cyclohexyladipates and adipic acid stream 17 recycled from the column base 5. The dissolution tank 1 may have an agitator 4. The primary feed stream 6 below the catalytic reaction section of the reactive distillation column will be a benzene, cyclohexene, and cyclohexane mixture from a benzene hydrogenation reactor. The overall mole ratio of adipic acid to cyclohexene fed to the process may vary from 0.5 to 1.0.

The benzene, cyclohexene, and cyclohexane feed stream 6 will enter the distillation column near the bottom, but at the top of a benzene, cyclohexene, and cyclohexane stripping section 8 consisting of 4–8 standard trays. Heat needed for column operation can be supplied by a heater-reboiler 16. Water 7 up to about 10% of the total hydrocarbon feed may be added at the base of the column stripping section to facilitate removal of the hydrocarbons from the tails stream 15. Added water can be decanted from the reactive distillation column overhead stream 12 and recycled to the base. The column tails stream 15 will contain primarily cyclohexyladipates and adipic acid.

Just above the point at which the benzene, cyclohexene, and cyclohexane feed is added to reactive distillation column will be a catalytic reaction section 9 consisting of 10–30 theoretical stages. The catalytic reaction section of the column will be packed with solid catalytic material consisting of an acid ion exchange resin, or an acidic zeolite, or other immobile catalytic materials known to catalyze formation of cyclohexyladipates from adipic acid and cyclohexene. In this section of the column, operated at a temperature of 120°–180° C., the rising cyclohexene vapors from the feed mixture will react selectively with an adipic acid stream 3 fed into the column near the top of the catalytic section and flowing countercurrently down through the catalyst. The adipic acid stream may contain other components such as cyclohexyladipates. The adipic acid stream may be partly or wholly a recycled stream obtained from the bottom of the column.

Just above the catalytic section of the column, and above the point of introduction of the adipic acid stream 3, will be a non-catalytic rectification section 13 consisting of 2–4 standard trays or equivalent packing material. This top section of the column will purify the benzene and cyclohexane vapors coming up the column, as well as any unreacted cyclohexene. Purified vapors leaving the top of the column at 10 will be condensed in a standard condenser 11. Any water fed to the system will be removed azeotropically and decanted at this point. A portion of the benzene, cyclohexane, and cyclohexene overhead be refluxed to the top tray. The remaining overhead condensate will be fed to the dissolver in 14 or recycled to the benzene hydrogenation process by way of 19.

The stripped adipic acid and cyclohexyladipates mixture produced at the bottom of the reactive distillation column will be enriched in cyclohexyladiapates and suitable for feed 18 to the nitric acid oxidation process for the manufacture of adipic acid. A portion of this stream will also be recycled to the dissolver in 17 and utilized as a solvent for the incoming adipic acid as described previously.

The preferred reactive distillation system would be designed for nearly complete reaction and removal of cyclohexene from the benzene hydrogenation hydrocarbon feed mixture, and for minimum amounts of adipic acid and mono-cyclohexyladipate in the stream fed to the nitric acid oxidation process. Benzene would be purified for return to the benzene hydrogenation step.

We claim:

1. A process for the production of cyclohexyladipates in a staged reaction zone containing an acid catalyst, said staged reaction zone having a upper portion and a lower portion, said staged reaction zone having a temperature above about 100 degrees C. and at a pressure greater than 20 psig, which comprises (a) feeding to the lower portion of the staged reaction zone a mixture containing a major amount of benzene, and a minor amount of cyclohexene, (b) feeding to the upper portion of the staged reaction zone, adipic acid, (c) removing cyclohexyladipates from the lower portion of the staged reaction zone, and (d) removing benzene from the upper portion of the staged reaction zone.

2. The process of claim 1 in which the staged reaction zone is a vertical distillation column.

3. The process of claim 1 in which the acid catalyst is selected from the group consisting of Bronsted and Lewis acids.

4. The process of claim 1 in which the acid catalyst is an acidic ion exchange resin, an acidic molecular sieve resin, or a heteropolyacid.

5. The process of claim 4 in which the acid catalyst is a Lewis acid and the Lewis acid is zinc dichloride.

6. The process of claim 1 in which the cyclohexyladipates are a mixture of mono and di-cyclohexyladipates.

7. A process of claim 1 in which the adipic acid is present in the reaction zone in an amount at least the stoichiometric amount necessary to form mono-cyclohexyladipate.

8. The process of claim 1 in which the reaction zone contains benzene and cyclohexene in a ratio of about 3 to 1 to about 6 to 1.

9. The process of claim 1 in which cyclohexene is present in a minor amount.

* * * * *